US006613175B1

(12) United States Patent
Moscherosch et al.

(10) Patent No.: US 6,613,175 B1
(45) Date of Patent: Sep. 2, 2003

(54) METHOD FOR MAKING AN ABSORBENT ARTICLE HAVING A LOW AUTOADHESION ATTACHMENT MEANS

(75) Inventors: Michael Moscherosch, Doylestown, PA (US); Joseph Michael Luizzi, Jr., Newtown, PA (US)

(73) Assignee: McNeil-PPC Inc., Skillman, NJ (US)

( * ) Notice: Subject to any disclaimer, the term of this patent is extended or adjusted under 35 U.S.C. 154(b) by 0 days.

(21) Appl. No.: 09/537,563

(22) Filed: Mar. 30, 2000

Related U.S. Application Data
(60) Provisional application No. 60/128,382, filed on Apr. 8, 1999.

(51) Int. Cl.⁷ ............................ A61F 13/15; B32B 31/00
(52) U.S. Cl. ............. 156/227; 604/385.03; 604/385.04; 604/385.201; 56/327
(58) Field of Search ........................ 156/227, 247, 156/327; 604/385.03, 385.04, 385.201, 390

(56) References Cited

U.S. PATENT DOCUMENTS

| | | | | |
|---|---|---|---|---|
| 4,136,699 A | * | 1/1979 | Collins | 128/290 |
| 5,217,448 A | * | 6/1993 | Glaug et al. | 604/397 |
| 5,459,193 A | | 10/1995 | Anderson et al. | |
| 5,670,004 A | * | 9/1997 | Mattingly, III | 156/227 |
| 5,743,897 A | | 4/1998 | Niihara et al. | 604/389 |
| 5,938,648 A | * | 8/1999 | LaVon et al. | 604/358 |

FOREIGN PATENT DOCUMENTS

| EP | 0525251 A1 * | 2/1993 | ........... A61L/15/58 |
|---|---|---|---|
| HU | P9501785 A | 12/1999 | |
| WO | WO 94/13237 A1 | 6/1994 | |

OTHER PUBLICATIONS

PCT International Search Report dated Sep. 1, 2000.
Hungarian Patent Office Novelty Search Report P 0201003 dated Apr. 10, 2002.

* cited by examiner

*Primary Examiner*—Michael W. Ball
*Assistant Examiner*—Todd J. Kilkenny

(57) ABSTRACT

The present invention relates to a method of applying a hot melt adhesive to an absorbent article, such that the article has low autoadhesion, yet maintains excellent attachment properties during use in a consumer's undergarments. This is achieved by selecting the rheological properties of the adhesive and the mechanical properties of the substrate being coated. The adhesive is directly applied to a backsheet layer outer surface, wherein the adhesive has a viscosity of less than about 10,000 centipoise at a temperature of about 130 to about 177 degrees Celsius. The backsheet layer has a tensile strength of at least 5 Newtons per 25 millimeter width of material.

20 Claims, 3 Drawing Sheets

METHOD FOR MAKING AN ABSORBENT ARTICLE HAVING A LOW AUTOADHESION ATTACHMENT MEANS

This application claims the benefit of Provisional Application No. 60/128,382, filed Apr. 8, 1999.

FIELD OF THE INVENTION

The present invention relates to a method for making absorbent articles comprising a backsheet layer having a low autoadhesion attachment means. The articles are capable of being folded and releasably affixed to themselves in the absence of a release liner. The articles of the present invention are particularly useful for managing bodily fluids, such as menses, urine, and perspiration. Sanitary napkins, pantiliners, ultrathins, incontinence devices, wound care and the like are included.

BACKGROUND OF THE INVENTION

Many absorbent articles, especially those designed and configured to absorb vaginal and/or urethral discharge, utilize pressure sensitive adhesive on a backsheet layer to attach the article to a user's undergarment. To protect the positioning adhesive prior to use, a releasable sheet is generally applied over the adhesive.

Release sheets have a number of disadvantages. The sheets are typically constructed from silicone coated paper, accounting for an expensive component in an absorbent article's composition. Moreover, consumers find it inconvenient and indiscreet to dispose of the sheet after removing it from the article.

Anderson et al., U.S. Pat. No. 5,459,193, discloses an approach for eliminating a separate release sheet by applying a hot melt adhesive to a garment-facing surface of an absorbent article that exhibits low self adhesion, and then folding the article upon itself. Anderson teaches the use of a high molecular weight S-EB-S (polystyrene-ethylene/butylene-polystyrene) block copolymer to form a positioning adhesive that is able to be removed from itself without destroying the article, while purportedly having superior stay-in-place properties. The adhesive formulation requires an S-EB-S copolymer having a molecular weight of greater than about 200,000.

Anderson also discloses, in its "Background of the Invention" section, that hot melt adhesives comprised of lower molecular weight block copolymers for purposes of adhering an absorbent article to an undergarment are known. However, Anderson also teaches that such adhesives are have such high self adhesion that the adhesive layers are separable only at the expense of destroying the article.

It has been found that a broader range of polymers can be utilized to make an absorbent article having a low autoadhesion attachment means, so long as the tensile strength of the backsheet layer is of a certain level and the viscosity of the adhesive is controlled within a certain range.

SUMMARY OF THE INVENTION

The present invention provides a method for making an absorbent article having a low autoadhesion attachment means for maintaining the article's position in use. The article is capable of being folded upon itself prior to use, and then unfolded without destroying any aspect thereof. The present invention eliminates the necessity of a separate release sheet to protect the positioning adhesive prior to use. This will eliminate non value-added costs, enhance consumer convenience by reducing the number of steps of use, enhance consumer discretion by eliminating release sheet handling issues such as noise and disposal, and reduce environmental concerns by eliminating a portion of the product from the solid waste stream.

One method provided by the present invention comprises the following steps: providing an absorbent article comprising a backsheet layer having a tensile strength of at least 5 Newtons per 25 millimeter width of material; directly applying a hot melt adhesive to the backsheet layer outer at a temperature of about 130 to about 177 degrees Celsius, wherein the adhesive has a viscosity of less than about 10,000 centipoise during application; and folding the article in a manner such that the article is releasably affixed to itself.

A second method provided by the present invention produces an absorbent article comprising lateral extensions having positioning adhesive thereon, capable of being releasably affixed to the backsheet.

BRIEF DESCRIPTION OF THE DRAWINGS

FIG. 1A depicts the article being directly coated with an adhesive, while FIG. 1B depicts the article folded and releasably affixed to itself.

DETAILED DESCRIPTION OF THE INVENTION AND THE PREFERRED EMBODIMENTS

The present invention relates to a method of applying a hot melt adhesive to an absorbent article, such that the article has low autoadhesion, yet maintains excellent attachment properties during use in a consumer's undergarments. This is achieved by selecting the rheological properties of the adhesive and the mechanical properties of the substrate being coated.

The articles produced by the present invention offer a number of advantages. First, the articles can be releasably affixed to themselves, thereby eliminating the need for a separate release sheet or a coated wrapper. The articles can be folded in a manner, wherein positioning adhesive is in contact with itself. When a user prepares to place the article in their undergarments, the article is unfolded such that the adhesive is not folded upon itself. Thereafter, the article is placed on the target surface.

Second, the articles will have reduced "bunching." This common consumer complaint creates permanent folds / creases in the article, rendering it uncomfortable and vulnerable to increased probability of peripheral leakage. The forces encountered between the article and the user's adjacent body parts and clothing can cause the article to distort. During the dynamics of bunching, the positioning adhesive can adhere to itself creating a permanent crease or fold. The present invention has reduced bunching by reducing the self-adherence of the positioning adhesive, allowing the article to "un-bunch." That is, the self-adhesion achieved with the invention is fully reversible.

Low autoadhesion configurations will also help to eliminate a common problem associated with articles having lateral extensions, such as tabs or wings. If a consumer is not careful, the lateral extensions just prior to placement in their undergarment can come into contact with positioning adhesive on the backsheet. One term used for this problem is "wing snapback." Articles employing conventional molecular weight styrenic based adhesives prior to this invention, would be rendered useless, since the force to separate the lateral extension from the backsheet would have exceeded the structural integrity of the article itself.

Figure 1A:
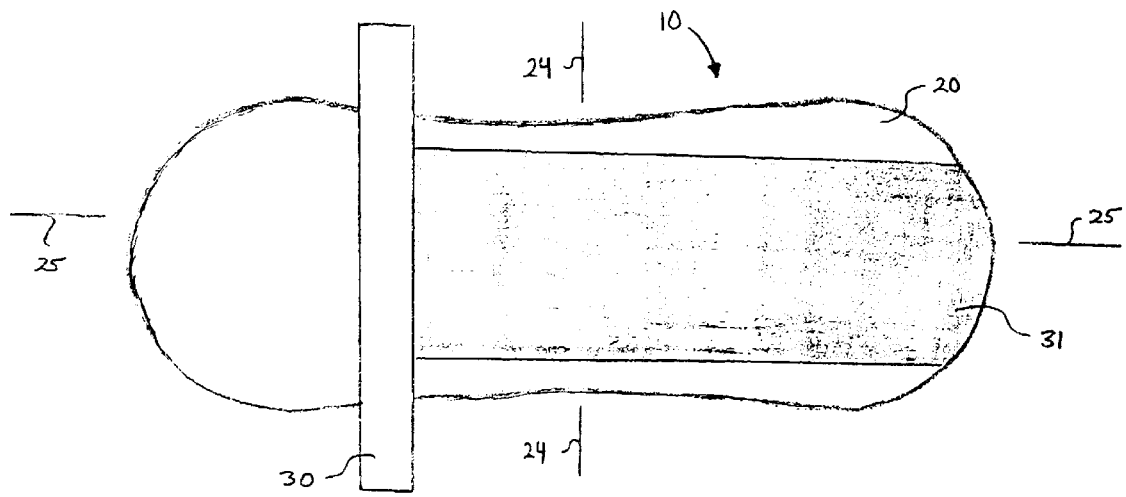
FIGS. 1A–1B is a diagram of a method of making a an absorbent article having a low autoadhesion attachment means.
Figure 1B:
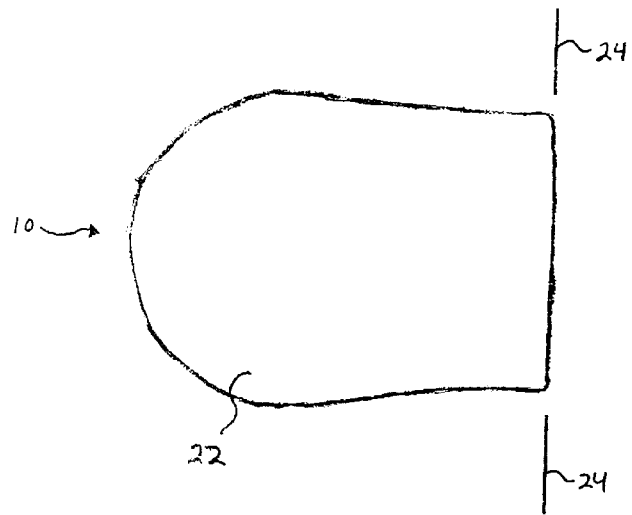

Preferred embodiments are shown in the figures, wherein like elements carry like numerical designations. FIGS. 1A–1B illustrate steps of making an absorbent article having a low autoadhesion attachment means. The absorbent article is direct coated with a hot melt adhesive, and then releasably folded onto itself.

Absorbent article 10 comprises a backsheet layer 20, the outer surface of which faces a user's undergarments; a cover layer 22, which in use faces the user's body; and absorbent material (not shown). Slot coating equipment 30 extrudes a film of hot melt adhesive 31 directly onto a portion of the outer surface of the backsheet layer 20. The article 10 is then folded in a manner wherein it is releasably affixed to itself.

One important aspect of the present invention is the structural integrity of the backsheet layer being coated with the hot melt adhesive. The backsheet layer preferably has a tensile strength of at least 5 Newtons per 25 millimeter width of material, as tested using the standardized method ASTM D-822. Many materials will exhibit anisotropic mechanical properties that are imparted during their manufacture. For example, the materials used for the backsheet layer may yield a different tensile strength value when tested in the machine direction compared to a cross direction. The lowest tensile strength value of a given material suitable for the present invention is within the preferred range above.

The backsheet layer may be a nonwoven, a polymeric film, monolithic film, or a lamination of multiple films. The nonwoven webs may comprise both synthetic and natural fibers and particles. The individual fibers / particles may be bonded by added binders, such as latex, or by heat; wherein the heat induces at least one polymeric component to flow sufficient to bind adjacent elements that are in contact. Preferred nonwovens are constructed from spunbond olefinic fibers and carded and heat bonded olefinic fibers. The preferred olefinic fibers are polypropylene. The nonwoven basis weight is ideally from about 15 to about 100 grams per square meter.

The most common material used as the backsheet layer in the industry is a polymeric film. The backsheet layer of the present invention may be a continuous, microporous, or apertured polymeric film. The films may optionally employ an embossed pattern.

A second important aspect of the present invention is the rheological properties of the adhesive as it is applied to the backsheet layer. Preferably, the adhesive has a viscosity less than about 10,000 centipoise at a temperature of about 130 to about 177 degrees Celsius; more preferably a viscosity from about 1,300 to about 5,000 centipoise at a temperature of about 160 to 170 degrees Celsius. Application of the adhesive at such a temperature and viscosity allows the adhesive to better "wet" the backsheet material and enhance mechanical interlocking to the substrate.

A common method of applying positioning adhesive to a backsheet layer is by first applying the adhesive to a release sheet and then transferring it to the backsheet. The present invention requires the adhesive to be directly applied to the backsheet layer. It would be extremely difficult, if not impossible, to obtain the preferred viscosity on contact with the substrate material if utilizing a transfer technique.

Any coating technique known to one having ordinary skill in the art may be used. Preferred techniques include slot coating, micro-fiber spraying, and filament spraying. The positioning adhesive add-on for the area coated is from about 0.75 to about 75 milligrams per square centimeter.

The hot melt adhesives useful for the present invention includes styrenic block copolymers. In a preferred embodiment, the adhesive is based on a high S-I-S (styrene-isoprene-styrene) block copolymer. Preferably the molecular weight is less than about 200,000, although polymers having a greater molecular weight will have utility as well. In addition to the polymer, the adhesive formulation will typically comprise a tackifying component, and a plasticizer. An adhesive formulation particularly suitable for the present invention comprises about 10 to about 30 percent by weight of a high S-I-S block copolymer, up to about 25 percent by weight of a plasticizer, and a about 45 to about 65 percent by weight of a tackifier.

Tackifiers useful in the adhesive formulation of the present invention include, but are not limited to rosin derivatives including wood rosin, tall oil, tall oil derivatives, rosin ester resins, natural and synthetic terpenes, and aliphatic aromatic or mixed aliphatic-aromatic tackifying resins. A representative, non-limiting, list of suitable plasticizers includes hydrocarbon oils, olefin oligomers, polybutene low molecular weight polymers, vegetable oils, and mineral oils.

FIG. 1B depicts article 10 in a bi-folded configuration, wherein the fold is along a transverse fold axis 24. This can be a final configuration or additional folds / rolling can take place, to maximize discreetness and portability. Folding and/or rolling the article makes it conducive to packaging it with an intravaginal device or an interlabial article, such as in a system of products to be used together.

Figure 2:
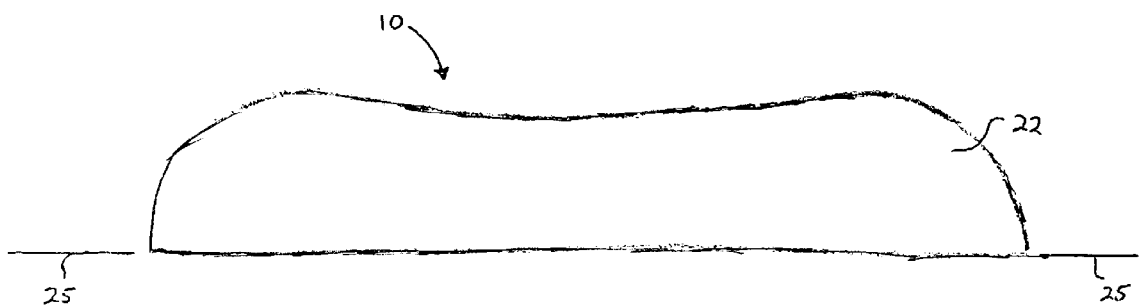
FIG. 2 is a plan view of an article of the present invention having been bi-folded lengthwise along a longitudinal fold axis.
Figure 3:
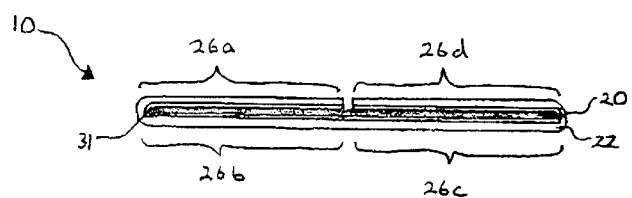
FIG. 3 is a side view of an article of the present invention been folded along two transverse fold axes and releasably affixed to itself.

An alternative embodiment, as shown in FIG. 2, is an article 10 bi-folded lengthwise along a longitudinal fold axis 25. FIG. 3 illustrates yet another embodiment, wherein article 10 consists of four substantially equal sections 26a–26d, and is at least initially folded along transverse fold axes such that the two end fourths 26a and 26d are folded inwardly onto the two middle fourths 26b and 26c.

The figures depict contoured absorbent articles. It should be readily appreciated to those of skill in the art, that depending on the peripheral geometry and the manner the article is folded, there may be material "overhang," wherein a portion of the backsheet is not in contact with another portion. To accomplish an objective of eliminating the need for a separate release sheet, articles designed in configured in this manner must employ adhesive coverage that is less than complete backsheet coverage.

The article of the present invention may optionally include lateral extensions, typically referred to as "wings" or "tabs." The lateral extensions are capable of being wrapped around the crotch portion of a user's undergarments to provide placement retention and protection benefits. A common problem associated with the use of articles having lateral extensions is that the extensions may "snap back" before affixing them to the undergarments. Positioning adhesive located on the lateral extensions then may come into contact with positioning adhesive on the backsheet layer of the article. The lateral extensions may not be separable from the backsheet without destroying the article. The present invention eliminates this concern, by coating the backsheet layer and optionally the outwardly disposed surfaces of optional lateral extensions with low autoadhesion adhesive coatings. If the lateral extensions do in fact contact the backsheet prior to placement in the undergarments, then the user simply peels them away.

Figure 4:
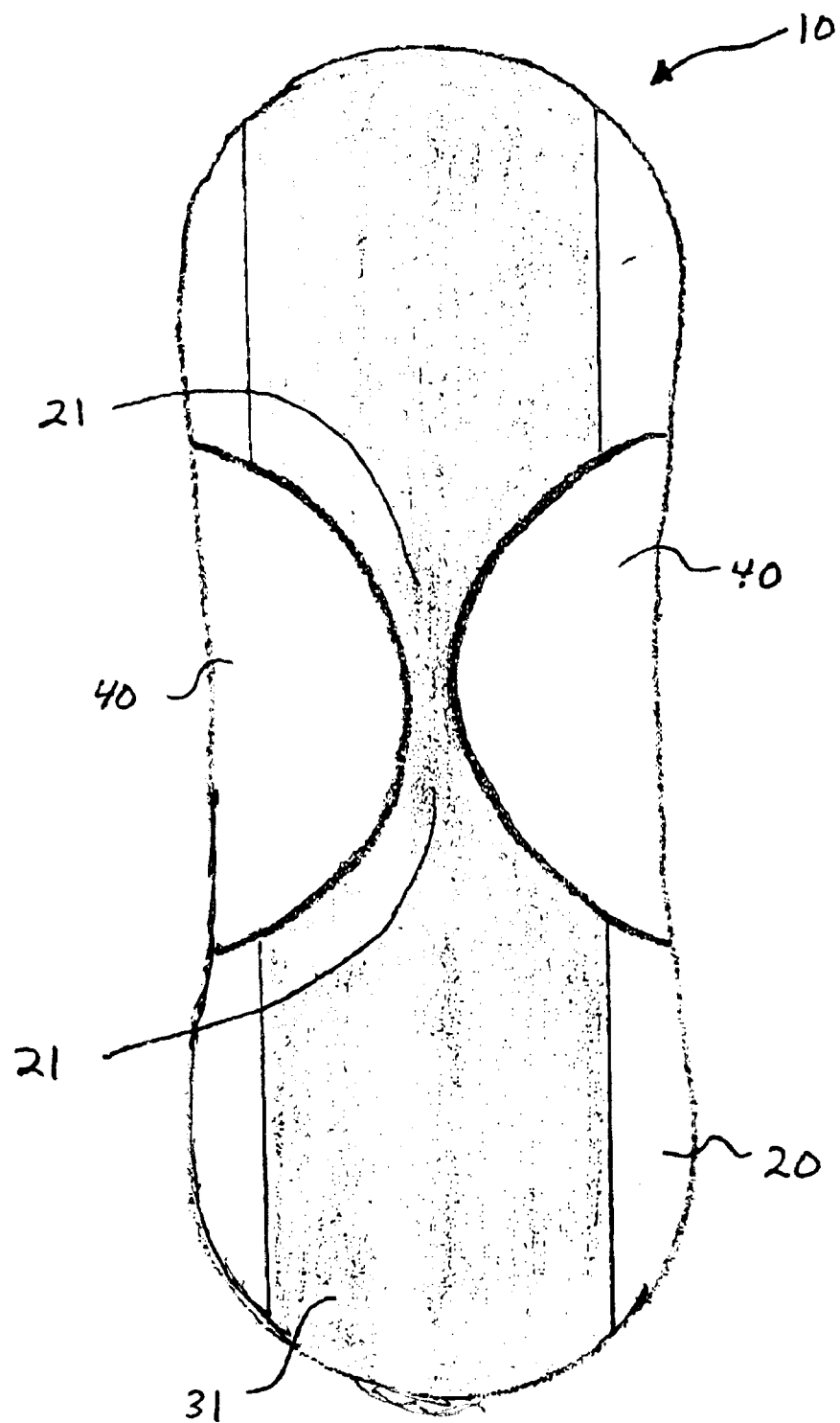
FIG. 4 is a plan view illustrating an article of the present invention employing optional lateral extensions, wherein the extensions are folded and releasably affixed to a central portion of the backsheet.

In addition to the utility of preventing snap back related problems, is the possibility of eliminating separate release sheets to protect the lateral extension positioning adhesive. This is accomplished by releasably affixing the extensions to a portion of the backsheet. The end user would purchase the articles in the described configuration and decide to utilize the lateral extensions, or alternatively leave them folded and utilize other provided attachment means. An example is illustrated in FIG. 4, wherein the article 10 comprises two lateral extensions 40 folded and releasably affixed to a backsheet central portion 21.

The absorbent articles of the present invention comprise a cover layer, a backsheet layer, and absorbent material. The cover layer is preferably compliant, soft feeling, and non-irritating to a user's skin. The cover layer should further exhibit good strikethrough and a reduced tendency to rewet, permitting bodily discharges to rapidly penetrate it and flow toward subsequent underlying layers, while not allowing such discharges to flow back through the cover to the skin of the user.

A suitable cover layer may be manufactured from a wide range of materials including, but not limited to woven and nonwoven fabrics, apertured formed polymeric films, hydroformed films, porous foams, reticulated foams, reticulated thermoplastic films, and thermoplastic scrims. In addition, the cover layer may be constructed from a combination of one or more of the above materials, such as a composite layer of nonwoven and apertured formed thermoplastic film.

Apertured films are well suited for the cover layer because they are pervious to liquids and, if properly apertured (including tapering), have a reduced tendency to allow liquids to pass back through and rewet the user's skin. Useful films are disclosed in the following U.S. Pat. Nos. 3,929,135; 4,324,426; 4,342,314; 4,463,045; and 5,006,394.

A representative, non-limiting list of absorbent material useful in the present invention includes natural cellulosics, such as cotton and wood pulp; regenerated cellulosics, such as rayon and cellulose acetate; peat moss; hydrogel-forming polymers in the form of fibers or particles, commonly referred to as "superabsorbents"; and the like. One of ordinary skill in the art would readily appreciate that a blend of two or more types of absorbent materials may be used to optimize the performance of absorbent articles used in varying conditions. The absorbent material may be uniformly dispersed, or may alternatively be placed in discrete patterns, or in gradients.

The absorbent material may be in the form of an absorbent core, i.e., a distinct layer intermediate the cover and backsheet layers. Alternatively, the cover or backsheet layer may comprise absorbent material within its structure, or on one or both of its surfaces, as a composite structure.

The individual layers of the present invention may employ any known assembly techniques for adhering adjacent layers together. A representative, non-limiting list of assembly techniques and materials, includes adhesives, heat seal, ultrasonic welding, solvent welding, and mechanical fastening. Preferably, construction adhesives are used to laminate individual elements to one another. Suitable construction adhesives are disclosed in the following U.S. Pat. Nos. 4,526,577; 5,149,741; and 5,057,571. The construction adhesives may be modified to be absorbing by incorporating absorbing polymer into their formulations.

The absorbent articles of the present invention may be of any shape suitable for placement against a user's perineum and the surrounding areas. Shapes include rectangular, oval, dogbone, peanut shape, and the like. Asymmetry with respect to the transverse ends may a useful shape as well, such as for use in "thong-type" undergarments.

The disclosures of all patents, as well as any corresponding published foreign patent applications, mentioned throughout this patent application are hereby incorporated by reference herein.

The specification and embodiments above are presented to aid in the complete and non-limiting understanding of the invention disclosed herein. Since many variations and embodiments of the invention can be made without departing from its spirit and scope, the invention resides in the claims hereinafter appended.

What is claimed is:

1. A method for making an absorbent article having a low autoadhesion attachment means, comprising the steps of:
   a) providing a low autoadhesion attachment means comprising an absorbent article comprising a backsheet layer having a tensile strength of at least 5 Newtons per 25 millimeter width of material and a hot melt adhesive comprising a S-I-S block copolymer, wherein the hot melt adhesive is directly applied to the backsheet layer outer surface at a temperature of about 130 to about 177 degrees Celsius and wherein the adhesive has a viscosity of less than about 10,000 centipoise during application and
   b) folding the article in a manner such that the article is releasably affixed to itself.

2. The method of claim 1 wherein the backsheet layer is a nonwoven.

3. The method of claim 2 wherein the nonwoven is selected from the group consisting of spunbonded polypropylene and carded polypropylene.

4. The method of claim 2 wherein the nonwoven has a basis weight of from about 15 to about 100 grams per square meter.

5. The method of claim 1 wherein the backsheet layer is a polymeric film.

6. The method of claim 5 wherein the polymeric film is embossed or apertured.

7. The method of claim 5 wherein the polymeric film is microporous.

8. The method of claim 1 wherein the adhesive is applied by a method selected from the group consisting of slot coating and micro-fiber spraying.

9. The method of claim 1 wherein the adhesive comprises:
   a) about 10 to about 30 percent by weight of a high S-I-S block copolymer;
   b) up to about 25 percent by weight of a plasticizer; and
   c) about 45 to about 65 percent by weight of a tackifier.

10. The method of claim 1 wherein the viscosity is from about 1300 to about 5000 centipoise.

11. The method of claim 1 wherein the article is at least initially bi-folded along a transverse fold axis.

12. The method of claim 1 wherein the article consists of four substantially equal sections, and is at least initially transversely folded such that two end fourths are folded inwardly onto two middle fourths.

13. The method of claim 1 wherein the article is at least initially bi-folded along a longitudinal fold axis.

14. A method of making an absorbent article having a low autoadhesion attachment means, comprising the steps of:
   a) providing a low autoadhesion attachment means comprising an absorbent article comprising a backsheet layer and lateral extensions, each of which have a tensile strength of at least 5 Newtons per 25 millimeter width of material and a hot melt adhesive comprising a S-I-S block copolymer, wherein the hot melt adhesive is directly applied to the outer surfaces of the backsheet layer and lateral extensions at a temperature of about 130 to about 177 degrees Celsius and wherein the adhesive has a viscosity of less than about 10,000 centipoise during application; and
   b) folding the lateral extensions so as to contact the backsheet layer, such that the lateral extensions are releasably affixed to the backsheet layer.

15. The method of claim 14 wherein the lateral extensions are releasably affixed to the central portion of the backsheet layer.

16. The method of claim 14 wherein the backsheet layer is a nonwoven.

17. The method of claim 14 wherein the adhesive comprises:
   a) about 10 to about 30 percent by weight of a high S-I-S block copolymer;
   b) up to about 25 percent by weight of a plasticizer; and
   c) about 45 to about 65 percent by weight of a tackifier.

18. The method of claim 14 wherein the viscosity is from about 1300 to about 5000 centipoise.

19. An absorbent article made by the method of claim 1.

20. An absorbent article made by the method of claim 14.

* * * * *